United States Patent
Schwartz et al.

(10) Patent No.: US 6,248,888 B1
(45) Date of Patent: *Jun. 19, 2001

(54) PROCESS FOR THE PREPARATION OF TERAZOSIN HYDROCHLORIDE DIHYDRATE

(75) Inventors: Eduard Schwartz; Marioura Mendelovici, both of Rehovot; Neomi Gershon, Rosh Ha'Ayin, all of (IL)

(73) Assignee: Teva Pharmaceutical Industries Ltd., Petah Tigva (IL)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/969,863

(22) Filed: Nov. 14, 1997

(51) Int. Cl.[7] ................................................. C07D 405/14
(52) U.S. Cl. ............................................................ 544/291
(58) Field of Search .............................................. 544/291

(56) References Cited

U.S. PATENT DOCUMENTS

| | | | |
|---|---|---|---|
| 4,026,894 | 5/1977 | Winn et al. | 260/256.4 |
| 4,112,097 | 9/1978 | Winn et al. | 424/251 |
| 4,243,666 | 1/1981 | Campbell et al. | 424/248.54 |
| 4,251,532 | 2/1981 | Roteman | 424/251 |
| 4,775,673 | 10/1988 | Koenig et al. | 514/254 |
| 5,212,176 | 5/1993 | Kyncl et al. | 514/254 |
| 5,294,615 | 3/1994 | Meyer et al. | 514/254 |
| 5,362,730 | 11/1994 | Bauer et al. | 514/254 |
| 5,412,095 | 5/1995 | Morley et al. | 544/291 |
| 5,504,207 | 4/1996 | Mannino et al. | 544/291 |
| 5,587,377 | 12/1996 | Patel et al. | 514/254 |
| 5,675,006 | 10/1997 | Karimian et al. | 544/283 |

FOREIGN PATENT DOCUMENTS

| | | |
|---|---|---|
| 2150985 | 12/1996 | (CA) . |
| 708104 | * 4/1996 | (EP) . |
| 2007656 | 5/1979 | (GB) . |
| 5-78352 | 3/1993 | (JP) . |
| WO-94/05628 | 3/1994 | (WO) . |

OTHER PUBLICATIONS

Database Chemical Abstracts on STN, American Chemical Society, (Columbus, OH, USA) Vol. 127, No. 318981, Ponge et al. "Solvent System for producing terazosin," abstract, HU 75100 A2, Apr. 28, 1987 (Hungarian).

* cited by examiner

Primary Examiner—Emily Bernhardt
(74) Attorney, Agent, or Firm—Kenyon & Kenyon

(57) ABSTRACT

A process for the preparation of 1-(4-amino-6,7-dimethoxy-2-quinazolinyl)-4-(2-tetrahydrofuroyl)piperazine hydrochloride dihydrate, and the product produced thereby, comprising reacting by heating 2-chloro-4-amino-6,7-dimethoxyquinazoline and 1-(2-tetrahydrofuroyl)piperazine in a polar organic reaction solution, wherein the polar organic reaction solution comprises a polar organic solvent and a minimum amount of water effective to produce 1-(4-amino-6,7-dimethoxy-2-quinazolinyl)-4-(2-tetrahydrofuroyl)piperazine hydrochloride dihydrate. The heat is added, preferably at reflux for a period of time, after which the reaction solution is allowed to cool to room temperature and the crystalline product 1-(4-amino-6,7-dimethoxy-2-quinazolinyl)-4-(2-tetrahydrofuroyl)piperazine hydrochloride dihydrate is filtered and dried.

10 Claims, 2 Drawing Sheets

PROCESS FOR THE PREPARATION OF TERAZOSIN HYDROCHLORIDE DIHYDRATE

FIELD OF THE INVENTION

Figure 1:
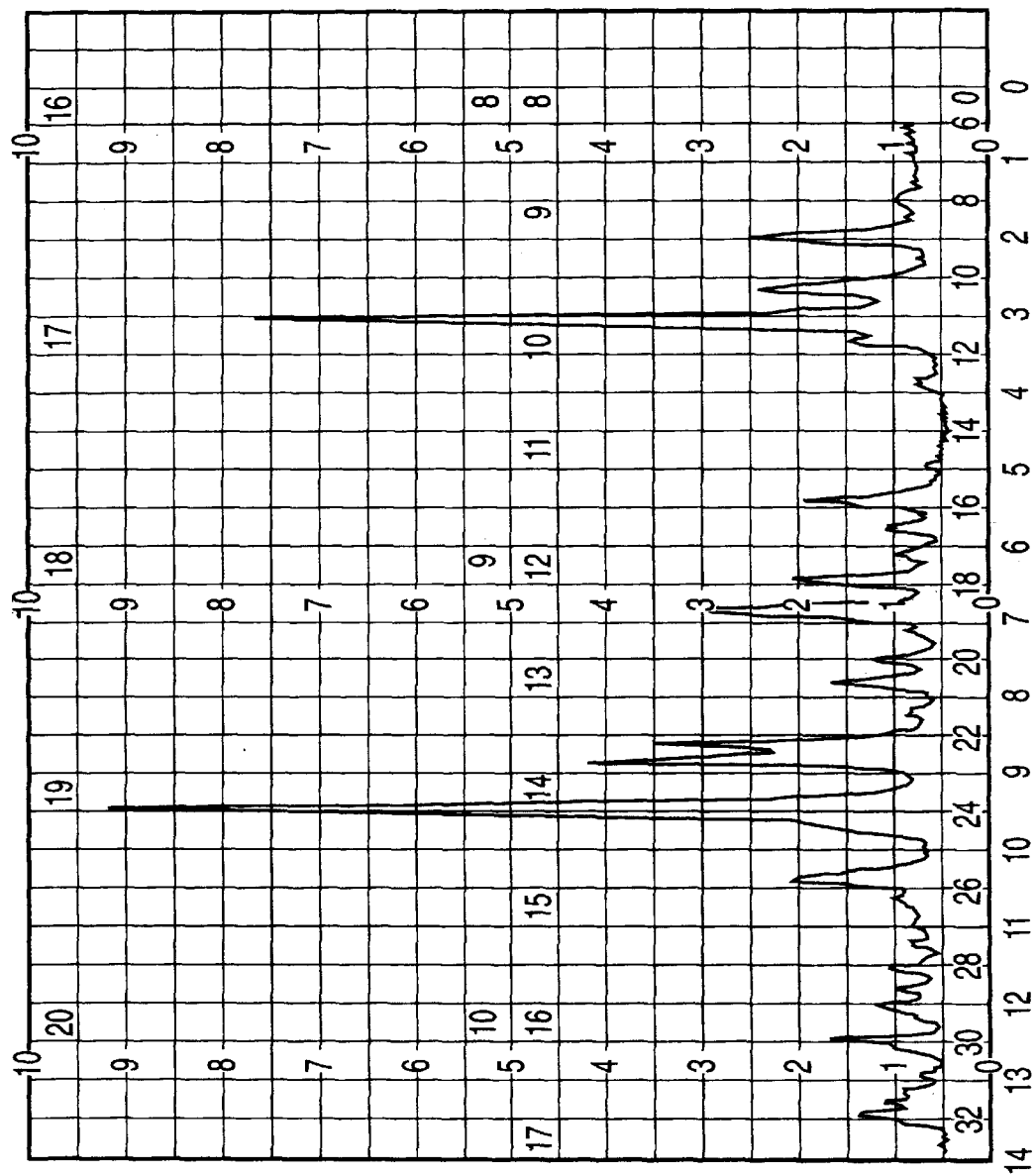

The present invention relates to a process for the preparation of 1-(4-amino-6,7-dimethoxy-2-quinazolinyl)-4-(2-tetrahydrofuroyl)piperazine hydrochloride dihydrate, hereinafter referred to as Terazosin.HCl dihydrate. More particularly, the present invention relates to a heretofore unknown one-step process for synthesizing Terazosin.HCl dihydrate and to the Terazosin.HCl dihydrate produced by the process.

BACKGROUND OF THE INVENTION 1-(4-amino-6,7-dimethoxy-2-quinazolinyl)-4-(2-tetrahydrofuroyl)piperazine hydrochloride ("terazosin hydrochloride") is disclosed in U.S. Pat. No. 4,026,894. The compound is used for the treatment of hypertension and benign prostatic hyperplasia. Pharmaceutical compositions comprising terazosin and its salts are disclosed in U.S. Pat. No. 4,112,097.

Terazosin hydrochloride exists in several polymorphic forms including non-solvated crystalline forms: Form I–Form IV, a methanolate form, a monohydrate crystalline form and a dihydrate crystalline form. Form I is disclosed in U.S. Pat. No. 4,026,894. Form II is disclosed in U.S. Pat. No. 5,294,615. Form III and the methanolate form are disclosed in U.S. Pat. No. 5,412,095. Form IV is disclosed in U.S. Pat. No. 5,504,207 and was also disclosed in published Japanese Patent Application No. 5-078352 as type A-2. A monohydrate form was disclosed in U.S. Pat. No. 5,587,377. Terazosin.HCl dihydrate is disclosed in U.S. Pat. No. 4,251,532, and is marketed under the trade name Hytrin©.

U.S. Pat. No. 4,251,532 describes a process for the preparation of Terazosin.HCl dihydrate which involves as an initial step the preparation of terazosin anhydrous base using an acid scavenger. In a further step, the base form is converted to Terazosin.HCl dihydrate by the addition of hydrochloric acid.

U.S. Pat. No. 5,504,207 also relates to a process for the preparation of Terazosin.HCl dihydrate. The disclosed multi-step process involves an initial step in which terazosin Form IV is first prepared in the absence of an acid scavenger. The Form IV is then converted by a second reaction to Terazosin.HCl dihydrate.

Canadian Pat. No. 2,150,985 describes a process for preparing Terazosin.HCl dihydrate which initially involves the preparation of terazosin free base. The free base form is then reacted by suspension in water and the addition thereto of a molar equivalent of aqueous hydrochloric acid to produce Terazosin.HCl dihydrate.

The known methods discussed hereinabove are not as industrially efficient or as commercially optimized as possible. Generally speaking, the references require various forms of terazosin for their initial step and subsequent processes steps are required to separate these forms from the reaction by-products. Then, one must still perform more work to convert these terazosin forms to Terazosin.HCl dihydrate. It is well known in industrial economics that every processing step usually adds to the complexity and thereby the cost of a process. Additional cost factors include increasing preparation time and increasing the volumes and types of materials which must be kept on hand as starting materials and as waste products of the process. Moreover, any Terazosin.HCl dihydrate process which calls for the conversion of terazosin introduces a possibility of having other terazosin forms as impurities in the product which must then be separated out.

OBJECTS AND SUMMARY OF THE INVENTION

It is therefore an object of the present invention to provide a novel one-step process for the preparation of Terazosin.HCl dihydrate and to provide the Terazosin.HCl dihydrate produced thereby.

It is a further object of the present invention to provide a novel process for the preparation of Terazosin.HCl dihydrate which is highly efficient.

It is another object of the present invention to provide a novel process for the preparation of Terazosin.HCl dihydrate which is less complex than known processes.

It is still another object of the present invention to provide a novel process for the preparation of Terazosin.HCl dihydrate which minimizes the level of non-dihydrate crystalline forms in the product.

It is yet another object of the present invention to provide a novel process for the preparation of Terazosin.HCl dihydrate which reduces the costs and labor associated with known processes.

It is yet a further object of the present invention to provide a novel process for the preparation of Terazosin.HCl dihydrate which reduces the use of highly corrosive, environmentally unfriendly materials and further reduces occupational hazards caused by using materials according to known processes.

These objectives and other objects not mentioned hereinabove are achieved by the process of the present invention in which Terazosin.HCl dihydrate is prepared directly in one simple and safe step. Terazosin.HCl dihydrate (Product) is as follows:

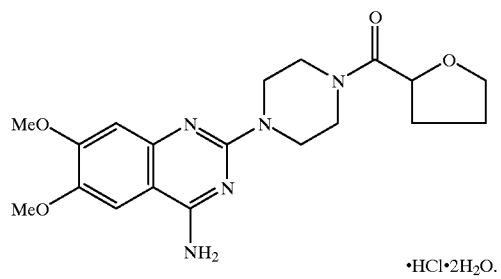

·HCl·2H$_2$O.

The process of the present invention comprises reacting by heating 2-chloro-4-amino-6,7-dimethoxyquinazoline (Reactant I):

Reactant I

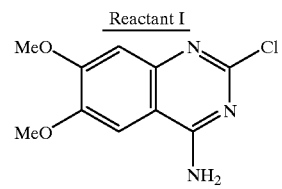

with 1-(2-tetrahydrofuroyl)piperazine (Reactant II)

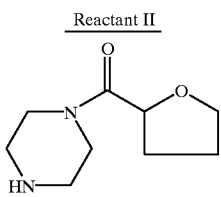

Reactant II in a polar organic reaction solution comprising a polar organic solvent and water. The water is present in a minimum amount effective to obtain the desired product, Terazosin.HCl dihydrate. The reaction mixture is then heated and preferably maintained at reflux until completion as determined by such monitoring methods as intermittent HPLC. The reaction solution is thereafter allowed to cool, preferably to room temperature, and the crystalline product material is collected by filtration.

BRIEF DESCRIPTION OF THE TABLE AND FIGURES

For a more complete understanding of the present invention, reference may be had to the following detailed description of exemplary embodiments taken in conjunction with the accompanying Figures entitled:

FIG. 1—X-Ray Diffraction of Terazosin.HCl dihydrate made by the process of the invention in accordance with Example 1 hereinbelow. Characteristic peaks at 2θ are seen at 8.8; 10.2; 11.0; 15.7; 17.7; 18.6; 20.0; 20.5; 22.1; 22.6; 23.9; and 25.7.

Figure 2:
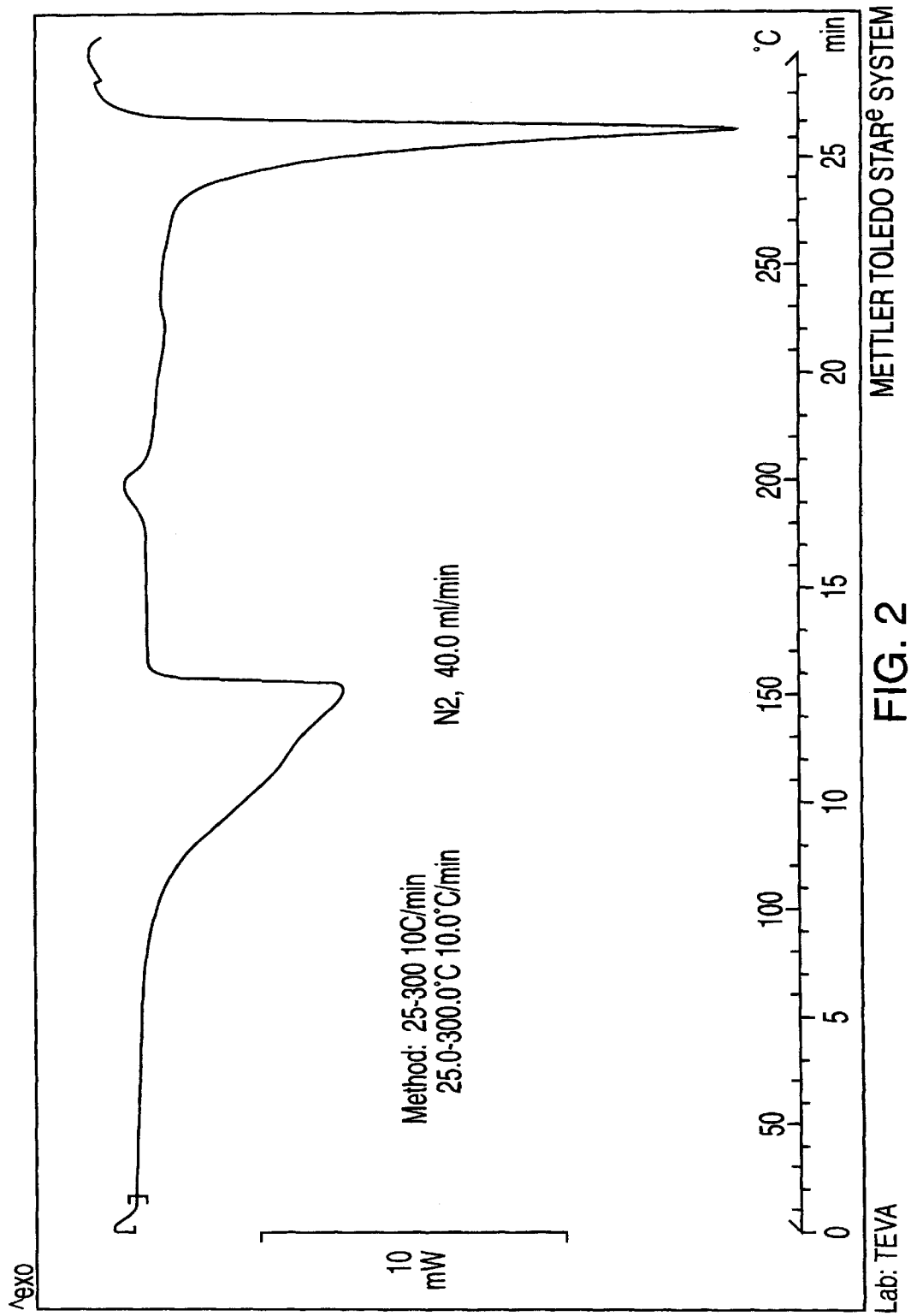

FIG. 2—DSC thermogram of Terazosin.HCl dihydrate made by the process of the invention in accordance with Example 1 hereinbelow. The thermogram is characterized by a broad endothermic dehydration peak below 200° C., a small exothermic peak at about 200° C. due to a phase transformation, and an endothermic peak at about 280° C. due to melting.

DETAILED DESCRIPTION OF THE INVENTION

As discussed hereinabove, the present invention relates to a simple one-step process for the preparation of Terazosin-.HCl dihydrate and the Terazosin.HCl dihydrate produced thereby. The process does not require the initial production of a different polymorph of terazosin which is subsequently converted to Terazosin.HCl dihydrate.

The process comprises adding 2-chloro-4-amino-6,7-dimethoxyquinazoline together with 1-(2-tetrahydrofuroyl)piperazine to a polar organic reaction solution comprising a polar organic solvent and water. The water is present in a minimum amount effective to obtain the desired product, Terazosin.HCl dihydrate. As can be seen from the exemplary embodiments, the minimum, effective amount of water can vary, depending on the polar organic solvent selected. In the Examples below, the percent volume of water which satisfactorily yielded the desired product ranged roughly from as little as 5% by volume to as much as 20% by volume and more. Other polar organic solvents may require a larger or smaller portion of water than the range demonstrated by the examples, but the determination thereof is well within the purview of one of ordinary skill in the art. The reaction mixture is then heated. Preferably, to ensure highest yields, the reaction mixture is maintained at reflux temperature for as much as 35–55 hours or until one or the other of the reactants is substantially consumed. The reaction mixture is thereafter allowed to cool, preferably to room temperature, and the crystalline Terazosin.HCl dihydrate is collected by filtration.

The practice of the present invention provides an efficient, high-yield one-step process for preparing Terazosin.HCl dihydrate from 2-chloro-4-amino-6,7-dimethoxyquinazoline and 1-(2-tetrahydrofliroyl)piperazine. Yields in the range of from 85 percent to about 95 percent and higher are routinely achieved by the inventive process.

The phrase, "minimum amount of water" is intended to signify the minimum percent volume of water which provides the appropriate conditions to produce Terazosin.HCl dihydrate from 2-chloro-4-amino-6,7-dimethoxyquinazoline and 1-(2-tetrahydrofuroyl) piperazine. Not intending to be bound by any particular theory regarding the mechanism of the inventive process, it is believed that the reaction proceeds as described to the dihydrate form only when a sufficient amount of water is dissolved into the reaction solution. Thus the miscibility of the water in the polar organic solvent appears to be an indicator as to what quantity of water will be required in the reaction solution.

As alluded to above, the successful practice of the present invention for the preparation of Terazosin.HCl dihydrate is also dependent on the type of the polar organic solvent. Different optimal water levels are required depending on the type of polar organic solvent used. For instance, consistent with the theory implicating miscibility as a factor, it appears that the extent of a solvent's polarity may affect the dissolution of water in the polar organic solvent and hence the ability of the reaction to proceed to the dihydrate form. Some adjustment may be required by the practitioner to determine the optimal water content for a particular polar organic solvent, however such is clearly well within the scope of one skilled in the art in view of the teachings of the present invention.

In the exemplary embodiments which follow, polar organic solvents have been selected from the group consisting of $C_2$–$C_6$ alkyl alcohols, $C_2$–$C_6$ aryl alcohols, $C_2$–$C_6$ ketones and $C_2$–$C_6$ ethers. More specifically, preferred embodiments utilize solvents selected from the group consisting of n-butyl alcohol, isobutyl alcohol, isopropyl alcohol, ethyl alcohol, cyclohexanol, methyl ethyl ketone and dioxane. This is not intended to be an exhaustive list of water-miscible polar organic solvents which may be used to practice the invention. As can be seen with reference to the Examples, the minimum water volume which must be added to each of the exemplary solvents, i.e., that which is sufficiently high to drive the reaction to produce the dihydrate form, differs depending on the particular organic solvent chosen.

Additionally, it can be seen that the choice of solvent affects the temperature and hence the time of reflux which is required for the reaction to proceed to completion, i.e. that point at which substantially all the starting materials have been consumed. The range of time to heat at reflux in the exemplary embodiments may extend from about 4 hours to as much as 55 hours, or until one or the other of the reactants is substantially completely consumed, as determined for example by HPLC. However, these times may vary with the specific conditions employed as one skilled in the art would recognize.

The crystalline form of Terazosin.HCl dihydrate which results from practicing the invention as exemplified herein is characterized by its X-ray diffraction pattern which is seen with reference to FIG. 1. The product of the process is further characterized by DSC thermogram data, for example, as disclosed in FIG. 2. The thermogram of FIG. 2 was produced using the Mettler Toledo Star® System.

The present invention will now be further explained in the following examples. However, the present invention should not be construed as limited thereby. Unless otherwise indicated, all parts, percentages and the like are by weight.

EXAMPLE 1

To a solution of n-butanol (316 ml), water (24 ml) and N-(2-tetrahydrofuroyl)piperazine (20 g) were added, while stirring, 4-amino-2-chloro-6,7-dimethoxyquinazoline (22.2 g). The reaction mixture was heated to reflux and the reflux was maintained for about 9 hours. Then the reaction mixture was cooled to room temperature and stirred at this temperature for about 10–12 hours. The crystals were collected by filtration, washed with n-BuOH and dried in vacuo at 40–50° C. to yield 40.1 g (94%) of Terazosin.HCl dihydrate. The product of this example was characterized by XRD and DSC melting point as shown in FIGS. 1 and 2 and in Table I as Trial H. This procedure was repeated in n-butanol using the water volumes indicated in Table I and yielding the results indicated for Trials G, I and J.

The procedure of the above example was repeated using solutions of iso-butanol (Trials A–F), iso-propanol (Trials K and L), ethanol (Trials M and N), cyclohexanol (Trial O), methyl ethyl ketone (Trial P) and dioxane (Trial Q), with various amounts of water as shown in Table I, hereinbelow. Table I tabulates the experimental results which have been achieved by following the method described hereinabove in Example 1 and as further described in the Examples hereinbelow.

EXAMPLE 2

To a solution of dioxane (155 ml), water (15 ml) and N-(2-tetrahydrofuroyl)piperazine (10 g) were added, while stirring, 4-amino-2-chloro-6,7-dimethoxyquinazoline (11.1 g). The reaction mixture was heated to reflux and the reflux was maintained for about 27 hours. Then the reaction mixture was cooled to room temperature and the crystals were collected by filtration and washed with dioxane. After drying in vacuo at 40° C., 20 g (93.8%) of Terazosin.HCl dihydrate was obtained. See Trial Q in Table I.

EXAMPLE 3

To a solution of iso-butanol (306 ml), water (34 ml) and N-(2-tetrahydrofuroyl)piperazine (20 g) were added, while stirring, 4-amino-2-chloro-6,7-dimethoxyquinazoline (22.2 g). The reaction mixture was heated to reflux and the reflux was maintained for about 13 hours. Then the reaction mixture was cooled to room temperature and stirred at this temperature for about 12 hours. The crystals were collected by filtration, washed with iso-butanol and dried in vacuo at 40° C. to yield 39.2 g (91.9%) of Terazosin.HCl dihydrate. See Trial A in Table I.

EXAMPLE 4

To a solution of iso-propanol (290 ml), water (50 ml) and N-(2-tetrahydrofuroyl)piperazine (20 g) were added, while stirring, 4-amino-2-chloro-6,7-dimethoxyquinazoline (22.2 g). The reaction mixture was heated to reflux and the reflux was maintained for about 35 hours. Then the reaction mixture was cooled to room temperature and stirred at this temperature for about 12 hours. The crystals were collected by filtration, washed with iso-propanol and dried in vacuo at 40° C. to yield 38.8 g (94%) of Terazosin.HCl dihydrate. See Trial K in Table I. Trial L was performed using a 5% percent volume of water.

EXAMPLE 5

To a solution of absolute ethanol (272 ml), water (68 ml) and N-(2-tetrahydrofuroyl)piperazine (20 g) were added, while stirring, 4-amino-2-chloro-6,7-dimethoxyquinazoline (22.2 g). The reaction mixture was heated to reflux and the reflux was maintained for about 32 hours. Then the reaction mixture was cooled to room temperature and stirred at this temperature for about 48 hours. The crystals were collected by filtration, washed with absolute ethanol and dried in vacuo at 40° C. to yield 36.44 g (85.5%) of Terazosin.HCl dihydrate. See Trial M in Table I. Trial N was performed using a 10% volume of water.

EXAMPLE 6

To a solution of cyclohexanol (78 ml), water (8 ml) and N-(2-tetrahydrofuroyl)piperazine (5 g) were added, while

TABLE I

| Trial | Polar Organic Solvent | % $H_2O$ in solvent | % Vol. of Quinazoline in the Polar Organic Reaction Solution ($V_{solution}:m_{quinazoline}$) | Results by XRD |
| --- | --- | --- | --- | --- |
| A | | 10% | 15 vol. | dihydrate |
| B | | 10% | 7.5 vol. | dihydrate |
| C | i-BuOH | 5% | 15 vol. | dihydrate |
| D | | 5% | 10 vol. | dihydrate + form II ~ 8:2 |
| E | | 3% | 15 vol. | form IV |
| F | | 1% | 15 vol. | form IV |
| G | | 9% | 15 vol. | dihydrate |
| H | n-BuOH | 7% | 15 vol. | dihydrate |
| I | | 5% | 15 vol. | dihydrate |
| J | | 3% | 15 vol. | form IV |
| K | IPA | 15% | 15 vol. | dihydrate |
| L | | 5% | 15 vol. | form II |
| M | EtOH | 20% | 7.5 vol. | dihydrate |
| N | | 10% | 15 vol. | form II + base |
| O | Cyclohexanol | 10% | 15 vol. | dihydrate |
| P | MEK | 8.5% | 15 vol. | dihydrate |
| Q | Dioxane | 9% | 15 vol. | dihydrate | stirring, 4-amino-2-chloro-6,7-dimethoxyquinazoline (5.55 g). The reaction mixture was heated to reflux and the reflux was maintained for at least 4 hours. Then the reaction mixture was cooled to room temperature and the product was filtered and washed with cyclohexanol and acetone. After drying in vacuo at 40° C., 9.4 g (88.5%) of Terazosin.HCl dihydrate was obtained. See Trial O in Table I.

EXAMPLE 7

To a solution of 8.5% water in methyl ethyl ketone (170 ml) were added N-(2-tetrahydroftiroyl)piperazine (10 g) and 4-amino-2-chloro-6,7-dimethoxyquinazoline (11 g). The reaction mixture was heated to reflux and the reflux was maintained for about 54 hours. After cooling to room temperature the product was filtered and dried in vacuo at 40° C. to give 18.3 g (85.7%) of Terazosin.HCl dihydrate. See Trial P in Table I.

A latitude of modification, change and substitution is intended in the foregoing disclosure. It should be understood that some modification, alteration and substitution is anticipated and expected from those skilled in the art without departing from the teachings of the invention. Accordingly, it is appropriate that the following claims be construed broadly and in a manner consistent with the scope and spirit of the invention.

What is claimed is:

1. A process for the preparation of 1-(4-amino-6,7-dimethoxy-2-quinazolinyl)-4-(2-tetrahydrofuroyl)piperazine hydrochloride dihydrate which comprises reacting by heating 2-chloro-4-amino-6,7-dimethoxyquinazoline and 1-(2-tetrahydrofuroyl)piperazine in a polar organic reaction solution, wherein said polar organic reaction solution comprises a polar organic solvent and a minimum amount of added water effective to produce said 1-(4-amino-6,7-dimethoxy-2-quinazolinyl)-4-(2-tetrahydrofiuroyl)piperazine hydrochloride dihydrate by precipitation.

2. A process for the preparation of 1-(4-amino-6,7-dimethoxy-2-quinazolinyl)-4-(2-tetrahydrofuroyl)piperazine hydrochloride dihydrate in accordance with claim 1, wherein said polar organic solvent is selected from the group consisting of $C_2-C_6$ alkyl alcohols, $C_2-C_6$ aryl alcohols, $C_2-C_6$ ketones and $C_2-C_6$ ethers.

3. A process for the preparation of 1-(4-amino-6,7-dimethoxy-2-quinazolinyl)-4-(2-tetrahydrofuroyl)piperazine hydrochloride dihydrate in accordance with claim 1, wherein said polar organic solvent is selected from the group consisting of isobutanol, n-butanol, iso-propyl alcohol, ethanol, cyclohexanol, methyl ethyl ketone and dioxane.

4. A process for the preparation of 1-(4-amino-6,7-dimethoxy-2-quinazolinyl)-4-(2-tetrahydrofuroyl)piperazine hydrochloride dihydrate in accordance with claim 1, in which said polar organic reaction solution containing said 2-chloro-4-amino-6,7-dimethoxyquinazoline and said 1-(2-tetra-hydrofuroyl)piperazine is heated at reflux for a determined time period.

5. A process for the preparation of 1-(4-amino-6,7-dimethoxy-2-quinazolinyl)-4-(2-tetrahydrofuroyl)piperazine hydrochloride dihydrate in accordance with claim 2, in which said polar organic reaction solution containing said 2-chloro-4-amino-6,7-dimethoxyquinazoline and 1-(2-tetrahydrofuroyl)piperazine is heated at reflux for a determined time period.

6. A process for the preparation of 1-(4-amino-6,7-dimethoxy-2-quinazolinyl)-4-(2-tetrahydrofuroyl)piperazine hydrochloride dihydrate in accordance with claim 4, wherein said time period is determined by measuring the amount of one of said 2-chloro-4-amino-6,7-dimethoxyquinazoline and 1-(2-tetrahydrofuroyl)piperazine.

7. A process for the production of 1-(4-amino-6,7-dimethoxy-2-quinazolinyl)-4-(2-tetrahydrofuroyl)piperazine hydrochloride dihydrate in accordance with claim 5, wherein said time period is determined by measuring the amount of one of said 2-chloro-4-amino-6,7-dimethoxyquinazoline and 1-(2-tetrahydrofuroyl)piperazine.

8. A process for the production of 1-(4-amino-6,7-dimethoxy-2-quinazolinyl)-4-(2-tetrahydrofuroyl)piperazine hydrochloride dihydrate in accordance with claim 4, wherein said time period is from 4 to 55 hours.

9. A process for the production of 1-(4-amino-6,7-dimethoxy-2-quinazolinyl)-4-(2-tetrahydrofuroyl)piperazine hydrochloride dihydrate in accordance with claim 5, wherein said time period is from 4 to 55 hours.

10. A process for the production of 1-(4-amino-6,7-dimethoxy-2-quinazolinyl)-4-(2-tetrahydrofuroyl)piperazine hydrochloride dihydrate in accordance with claim 1, wherein said 1-(4-amino-6,7-dimethoxy-2-quinazolinyl)-4-(2-tetrahydrofuroyl)-piperazine hydrochloride dihydrate is produced from said process in a yield of at least 90%.

* * * * *